United States Patent [19]

Nakamura et al.

[11] 4,313,875
[45] Feb. 2, 1982

[54] PURIFICATION OF PENICILLIN DERIVATIVE

[75] Inventors: Etsumi Nakamura, Toyonaka; Takashi Suzuki, Kawanishi; Tadasu Yanagida, Toyonaka; Minehiko Yamamura, Itami, all of Japan

[73] Assignee: Tanabe Seiyaku Co., Ltd., Osaka, Japan

[21] Appl. No.: 181,750

[22] Filed: Aug. 27, 1980

[30] Foreign Application Priority Data

Sep. 11, 1979 [JP] Japan .................................. 54-117030

[51] Int. Cl.$^3$ ............................................. C07D 499/68
[52] U.S. Cl. .................................... 260/239.1; 424/271
[58] Field of Search ....................................... 260/239.1

[56] References Cited

U.S. PATENT DOCUMENTS 4,053,609  10/1977  Kawazu et al. ................... 260/239.1
4,206,218   6/1980  Brown et al. ..................... 260/239.1

Primary Examiner—Natalie Trousof
Assistant Examiner—Vera C. Clarke

Attorney, Agent, or Firm—Bierman & Bierman

[57] ABSTRACT

Crude 6-[D-2-(D-2-amino-3-N-methylcarbamoyl-propionamido)-2-p-hydroxyphenylacetamido]penicillanic acid can be purified by the steps of:

(A) contacting an aqueous solution of 6-[D-2-(D-2-amino-3-N-methylcarbamoyl-propionamido)-2-p-hydroxyphenylacetamido]-penicillanic acid with a nonpolar, macroporous styrenedivinylbenzyl copolymer adsorption resin to adsorb 6-[D-2-(D-2-amino-3-N-methylcarbamoyl-propionamido)-2-p-hydroxyphenylacetamido]penicillanic acid on the resin, (B) eluting the adsorbed 6-[D-2-(D-2-amino-3-N-methylcarbamoyl-propionamido)-2-p-hydroxyphenylacetamido]penicillanic acid with water or a mixture of water and a water-miscible organic solvent, and then (C) isolating pure 6-[D-2-(D-2-amino-3-N-methylcarbamoyl-propionamido)-2-p-hydroxyphenylacetamido]penicillanic acid from the eluates.

17 Claims, 3 Drawing Figures

PURIFICATION OF PENICILLIN DERIVATIVE

This invention relates to a method for purification of 6-[D-2-(D-2-amino-3-N-methylcarbamoyl-propionamido)-2-p-hydroxyphenylacetamido]penicillanic acid (hereinafter simply referred to as "N'-methyl-D-asparaginylamoxicillin").

N'-methyl-D-asparaginylamoxicillin is a semi-synthetic penicillin which shows a potent inhibitory activity against gram-negative and gram-positive microorganisms. It has been known that N'-methyl-D-asparaginylamoxicillin can be prepared either (i) by condensing 6-aminopenicillanic acid with D-2-(D-2-amino-3-N-methylcarbamoyl-propionamido)-2-p-hydroxyphenylacetic acid or (ii) by condensing amoxicillin with D-2-amino-3-methylcarbamoyl-propionic acid (U.S. Pat. No. 4,053,609). However, N'-methyl-D-asparaginylamoxicillin prepared by the above-mentioned methods is inevitably contaminated with impurities such as by-products, starting materials and so forth, and this consequently needs its further purification for the medicinal use. To be more specific with said impurities, for example, D-2-(D-2-amino-3-N-methylcarbamoyl-propionamido)-2-p-hydroxyphenylacetic acid (hereinafter referred to as "impurity (A)"), penicilloic acid (hereinafter referred to as "impurity (B)"), the condensate of penicilloic acid and N'-methyl-D-asparaginylamoxicillin (hereinafter referred to as "impurity (C)"), and colored substances of unknown structure (hereinafter referred to as "impurity (D)") are contained in N'-methyl-D-asparaginylamoxicillin prepared by the method (i), and the impurities (B), (C) and (D) and amoxicillin (hereinafter referred to as "impurity (E)") are contained in N'-methyl-D-asparaginylamoxicillin prepared by the method (ii).

Heretofore, penicillins and cephalosporins have been purified by chromatography on the column of activated charcoal, alumina, ion exchange resins (e.g., Amberlite CG-400, Amberlite IRA-93, Diaion WA-21, Amberlite IR-45), ion exchange polysaccharides (e.g., diethylaminoethylcellulose) or Sephadex. However, since the physico-chemical properties of the above-mentioned impurities (A) through (E) are quite similar to those of N'-methyl-D-asparaginylamoxicillin, it is difficult to achieve a satisfactory removal of said impurities by these known methods. For example, when the purification of crude N'-methyl-D-asparaginylamoxicillin is carried out on the column of activated charcoal, said product is eluted almost simultaneously with the impurities (A) or (E), followed by elution of the impurities (B) and (C). On the other hand, when the purification of crude N'-methyl-D-asparaginylamoxicillin is carried out by the use of a weak anion exchange resin such as Diaion WA-10, Diaion WA-21, Amberlite IRA-93 and Amberlite IR-45, the impurities (A) or (E) and sometimes the impurities (B), (C) and/or (D) are eluted together with the major portion of said product. Thus, activated charcoal and the weak anion exchange resin are ineffective for the recovery of N'-methyl-D-asparaginylamoxicillin in high purity. Moreover, while the chromatography on the column of alumina is useful to remove the impurities (C) and (D) from crude N'-methyl-D-asparaginylamoxicillin, the impurities (A), (B) and (E) can not be separated from said product by alumina chromatography. Further, strong anion exchange resins can be used to remove the impurities (B), (C) and (D) from crude N'-methyl-D-asparaginylamoxicillin, but not to remove the impurities (A) or (E) therefrom. The use of Sephadex or the ion exchange polysaccharides also results in unsuccessful separation of the impurities from N'-methyl-D-asparaginylamoxicillin and, in this case, as much as 400 to 600 ml of these adsorbents must be used for purification of one g of crude N'-methyl-D-asparaginylamoxicillin (purity: about 80%).

An object of the present invention is to provide a simple and practical method for purification of N'-methyl-D-asparaginylamoxicillin. Another object of the invention is to provide a method for purification of N'-methyl-D-asparaginylamoxicillin by using a nonpolar macroporous adsorption resin of a styrene-divinylbenzene copolymer. A further object of the invention is to provide a method of removing the impurities stemming from the synthesis of N'-methyl-D-asparaginylamoxicillin. A still further object is to provide a method which enables recovery of N'-methyl-D-asparaginylamoxicillin in a high purity and in a high yield by a simple adsorption-elution operation. These and other objects of the present invention will become apparent from the following description.

In the accompanying drawings.

According to the present invention, crude N'-methyl-D-asparaginylamoxicillin can be purified by the steps of:

(A) contacting an aqueous solution of N'-methyl-D-asparaginylamoxicillin with a nonpolar, macroporous styrene-divinylbenzene copolymer adsorption resin to adsorb N'-methyl-D-asparaginylamoxicillin on the resin;

(B) eluting the adsorbed N'-methyl-D-asparaginylamoxicillin with water or a mixture of water and a water-miscible organic solvent; and then (C) isolating the pure N'-methyl-D-asparaginylamoxicillin from the eluates.

Nonpolar macroporous adsorption resins of styrene-divinylbenzene copolymers (i.e., polystyrene cross-linked with divinylbenzene) having a pore volume of 0.6 to 1.1 ml/g are suitable for use in the present invention. The specific surface area of said resin should preferably be within the range of 200 to 800 m$^2$/g, especially 300 to 750 m$^2$/g. Moreover, it is preferred that the nonpolar macroporous resins to be used in the present invention have a particle size of 45 to 840$\mu$, especially 70 to 370$\mu$. Representative examples of such copolymers include a styrene-divinylbenzene copolymer having pore volume of 0.890 ml/g, specific surface area of 501.3 m$^2$/g and particle size of 280 to 370$\mu$ (manufactured by Mitsubishi Chemical Industries Ltd. under the trade name of "Diaion HP-10"); a styrene-divinylbenzene copolymer having pore volume of 1.077 ml/g, specific surface area of 718.0 m$^2$g/ and particle size of 280 to 370$\mu$ (manufactured by Mitsubishi Chemical Industries Ltd. under the trade name of "Diaion HP-20"); a styrene-divinylbenzene copolymer having pore volume of 0.990 ml/g, specific surface area of 570 m$^2$/g and particle size of 280 to 370$\mu$ (manufactured by Mitsubishi Chemical Industries Ltd. under the trade name of "Diaion HP-30"); a styrene-divinylbenzene copolymer having pore volume of 0.687 ml/g, specific surface area of 704.7 m²/g and particle size of 280 to 370μ (manufactured by Mitsubishi Chemical Industries Ltd. under the trade name of "Diaion HP-40"); a styrene-divinylbenzene copolymer having pore volume of 0.693 ml/g, specific surface area of 300 m²/g and particle size of 280 to 840μ (manufactured by Rohm & Haas Co. under the trade name of "Amberlite XAD-2"); and a styrene-divinylbenzene copolymer having pore volume of 0.998 ml/g, specific surface area of 200 m²/g and particle size of 280 to 840μ (manufactured by Rohm & Haas Co. under the trade name of "Amberlite XAD-4"). While the adsorption and elution steps of the present invention may be performed batch-wise, it is preferred to carry out said steps continuously in a column.

The adsorption step of the present invention can be readily accomplished by passing an aqueous solution of crude N'-methyl-D-asparaginylamoxicillin through a column packed with the nonpolar, macroporous styrene-divinylbenzene copolymer adsorption resin. The resin which is used in the present invention is swollen with water beforehand. The volume of the resin to be used may vary over a wide range depending on the concentration of N'-methyl-D-asparaginylamoxicillin contained in an aqueous solution thereof or on the volume of said aqueous solution which is passed through the column. In general, however, it is preferred to use 3 to 100 ml, especially 30 to 80 ml, of the resin per gram of N'-methyl-D-asparaginylamoxicillin present in the aqueous solution thereof. It is also preferred to pass the aqueous solution through the column at a space velocity of 0.1 to 5, especially 0.3 to 2. The adsorption step may be preferably carried out at a temperature of 2° to 15° C., especially 4° to 6° C. In carrying out the above-mentioned adsorption step, it is preferred to use an aqueous solution containing 0.5 to 25 w/v %, especially 10 to 15 w/v % of N'-methyl-D-asparaginylamoxicillin. Such aqueous solution may be prepared in a conventional manner, for example, by dissolving crude N'-methyl-D-asparaginylamoxicillin in water, and, if required, further treating the solution with activated charcoal or filtering it to remove insoluble materials.

The elution step of the invention is readily accomplished by the use of water or a mixture of water and a water-miscible organic solvent. Namely, the elution of N'-methyl-D-asparaginylamoxicillin adsorbed on the resin is carried out by passing water or a mixture of water and the water-miscible organic solvent through the column at a space velocity of 0.3 to 15, especially 0.5 to 5. For example, when water is used as the eluant, it is preferred to pass water through the column at a space velocity of 0.3 to 15, especially 0.5 to 5. In this case, the impurities (A) (or (E)) and (B) are first liberated completely into eluates before the desorption of N'-methyl-D-asparaginylamoxicillin takes place, and, thereafter, N'-methyl-D-asparaginylamoxicillin is eluted gradually from the column by continuing the elution of the column with water. Thus, an aqueous solution of pure N'-methyl-D-asparaginylamoxicillin is obtained by collecting the eluates or fractions containing said compound. In this connection, the eluates or fractions containing N'-methyl-D-asparaginylamoxicillin can be readily distinguished from those containing the impurities, because N'-methyl-D-asparaginylamoxicillin present in the eluates can be detected by assaying the ultraviolet absorption of each eluates at 272 nm. Among the above-mentioned impurities (A) through (E), the impurities (C) and (D) remain adsorbed on the resin during the step of eluting N'-D-asparaginylamoxicillin from the column or even by further washing the column with water.

On the other hand, when the mixture of water and a water-miscible organic solvent is used as the eluant, the elution step is preferably carried out by passing said mixture through the column at a space velocity of 0.3 to 5, especially 1 to 3. In this case it is especially preferred that, prior to the elution with said aqueous mixture, the nonpolar macroporous resin having crude N'-methyl-D-asparaginylamoxicillin adsorbed thereon is washed with water to remove the impurities (A) (or (E)) and (B) beforehand. This washing step is carried out by passing water through the column of said resin at a space velocity of 0.1 to 5. Suitable examples of the mixture of water and a water-miscible organic solvent include a mixture of water and an alkanol having one to 4 carbon atoms (e.g., methanol, ethanol), a mixture of water and an alkanone having 3 to 4 carbon atoms (e.g., acetone, methyl ethyl ketone), a mixture of water and a dialkyl ether having 2 to 4 carbon atoms (e.g., dimethyl ether, diethyl ether), a mixture of water and a cyclic alkyl ether having 4 carbon atoms (e.g., tetrahydrofuran, dioxane), a mixture of water and a N,N-dialkyl alkanoylamide having 3 to 4 carbon atoms (e.g., dimethylformamide, dimethylacetamide) and a mixture of water and dimethylsulfoxide. Among them, a mixture of water and an alkanol having one to 3 carbon atoms is especially suitable for use in the present invention. In particular, the use of one to 15 v/v % (or more preferably 2 to 8 v/v %) aqueous methanol or aqueous ethanol is effective to rapidly elute N'-methyl-D-asparaginylamoxicillin from the column and give high recovery yields thereof. Concomitantly, the impurities (C) and (D) show no substantial desorption from the column during elution thereof with said aqueous mixture.

In any one of the above-mentioned cases, the elution step may be preferably carried out at a temperature of 2° to 15° C., especially 4° to 6° C. Moreover, when the elution of crude N'-methyl-D-asparaginylamoxicillin adsorbed on the styrene-divinylbenzene copolymer adsorption resin is carried out by the use of water or the mixture of water and a water-miscible organic solvent, the impurities (A) (or (E)) and (B) contained in said crude product are liberated completely into eluates before the desorption of N'-methyl-D-asparaginylamoxicillin takes place. On the other hand, the impurities (C) and (D) once adsorbed on the styrene-divinylbenzene copolymer adsorption resin are not liberated into eluates even by repeating the elution with water or the mixture of water and a water-miscible organic solvent several times. Therefore, an aqueous solution of N'-methyl-D-asparaginylamoxicillin which is substantially free from the impurities can be readily obtained by collecting the eluates or fractions containing said compound.

The isolation of N'-methyl-D-asparaginylamoxicillin from the aqueous solution obtained above may be accomplished by conventional methods. For example, N'-methyl-D-asparaginylamoxicillin is recovered in a high purity by condensation, freeze concentration, concentration by reverse osmosis, and/or freeze drying of said aqueous solution.

According to the method of the present invention, various impurities stemming from the synthesis of N'-methyl-D-asparaginylamoxicillin are removed quite efficiently from said compound by the simple adsorption-elution operation on the column of the nonpolar macroporous adsorption resin. In addition, since the purification step of the invention can be carried out without substantial decomposition of N'-methyl-D-asparaginylamoxicillin, said compound substantially free from the impurities can be recovered in a high yield.

The following Experiment and Examples further illustrate the present invention in detail but should not be construed to limit the scope thereof. In the Experiment and Examples, the high-performance liquid chromatography was performed under the following conditions.

Condition (A)

Column: stainless steel column (150 mm × 4 mm)
Packing agent: octadecyltrichlorosilane chemically bonded to 5-μm silica gel
Mobile phase: methanol-pH 5.5 phosphate buffer (12.5:87.5 v/v)
Flow rate: 0.5 ml/minute

Condition (B)

The high-performance liquid chromatography was carried out under the same conditions as described in Condition (A) except that methanol-pH 5.5 phosphate buffer (2.5:97.5 v/v) was employed as the mobile phase.

Concomitantly, the chemical structure of the impurity (B) described in the specification is shown as follows.

On the other hand, the impurity (C) described in the specification was decided to have the following chemical structure in view of its analytical data such as IR-spectrum, UV-spectrum, NMR-spectrum and elemental analysis thereof.

or adsorbent. Then, the column was eluted with water, and the fractions containing N'-methyl-D-asparaginylamoxycillin were collected. The impurities contained in said fractions as well as the purity and recovery yield of N'-methyl-D-asparaginylamoxicillin were examined by high-performance liquid chromatography (Condition A).

Resin or adsorbent (I): Styrene-divinylbenzene copolymer (pore volume: 1.077 ml/g, specific surface area: 718 m²/g, particle size: 280 to 370μ) (manufactured by Mitsubishi Chemical Industries Ltd. under the trade name of "Diaion HP-20")

(II): Strong anion exchange resin (polystyrene substituted with trimethylammonium group: $-N^+(CH_3)_3$) (manufactured by Rohm & Haas Co. under the trade name of "Amberlite CG-400")

(III): Weak anion exchange resin (divinylbenzene-acryl dimethylaminoalkylamide (i.e., $CH_2=CH-CONH(CH_2)_n-N(CH_3)_2$) copolymer) (manufactured by Mitsubishi Chemical Industries Ltd. under the trade name of "Diaion WA-10")

(IV): Weak anion exchange resin (polystyrene substituted with dimethylamino group: $-N(CH_3)_2$) (manufactured by Rohm & Hass Co. under the trade name of "Amberlite IRA-93")

(V): Weak anion exchange resin (styrene-divinylbenzene copolymer substituted with N-(polyiminoethylene)aminoethyl group: $-CH_2NH(CH_2CH_2NH)_nH$) (manufactured by Mitsubishi Chemical Industries Ltd. under the trade name of "Diaion WA-21")

(VI): Dextran gel cross-linked with epichlorohydrin (manufactured by Pharmacia Fine Chemicals Co. under the trade name of "Sephadex G-10")

(VII): Diethylaminoethylcellulose (VIII): Alumina (IX): Weak anion exchange resin (polystyrene substituted with primary, secondary and/or tertiary amino groups) (manufactured by Rohm & Haas Co. under the trade name of "Amberlite IR-45")

(B) Results

The results are shown in the following Table; i.e. it is clear from said Table that in the method of the present invention the impurities (A) and (B) were liberated

Experiment (A) Method

An aqueous solution of crude N'-methyl-D-asparaginylamoxicillin (purity: 79%), which was prepared in the same manner as described in Example 1-(A), was passed through a column packed with a resin completely into the eluates before the desorption of N'-methyl-D-asparaginylamoxicillin took place, and the impurities (C) and (D) remained adsorbed on the resin during the elution of N'-methyl-D-asparaginylamoxicillin with water. Thus, N'-methyl-D-asparaginylamoxicillin substantially free from these impurities could be recovered almost quantitatively. Unlike the method of the present invention, however, N'-methyl-D-asparaginylamoxicillin could not be separated from the impurity (A) by the use of the adsorbents (II), (III), (IV), (VI) and (VII) because both substances were eluted almost simultaneously. Where alumina (VIII) was used, the impurities (A) and (B) were eluted together with N'-methyl-D-asparaginylamoxicillin. In the case of the anion exchange resin (V), the impurities (A), (B) and (C) were eluted together with N'-methyl-D-asparaginylamoxicillin. Further, where the anion exchange resin (IX) was used, all of N'-methyl-D-asparaginylamoxicillin and the impurities (A) through (D) were eluted almost simultaneously.

TABLE

| Resins or adsorbents | N'-methyl-D-asparaginyl amoxicillin | Components in the fractions* | | | | Purity** (%) | Recovery yield** (%) |
|---|---|---|---|---|---|---|---|
| | | Impurities | | | | | |
| | | A | B | C | D | | |
| (The method of the present invention) | | | | | | | |
| (I) | (+) | (−) | (−) | (−) | (−) | 100 | 97.0 |
| (Control) | | | | | | | |
| (II) | (+) | (+) | (−) | (−) | (−) | 85.0 | 20.0 |
| (III) | (+) | (+) | (−) | (−) | (−) | 93.0 | 18.6 |
| (IV) | (+) | (+) | (−) | (−) | (−) | 95.0 | 52.3 |
| (V) | (+) | (+) | (+) | (+) | (−) | 88.0 | 47.5 |
| (VI) | (+) | (+) | (−) | (−) | (−) | 90.0 | 73.0 |
| (VII) | (+) | (+) | (−) | (−) | (−) | 47.0 | 56.0 |
| (VIII) | (+) | (+) | (+) | (−) | (−) | 87.0 | 37.0 |
| (IX) | (+) | (+) | (+) | (+) | (+) | 81.0 | 86.0 |

Note:
*(+): The component in question was contained in the fractions collected. (−): The component in question was not contained in the fractions collected.
**The purity and recovery yield of N'-methyl-D-asparaginyl amoxicillin were estimated based on the following fractions collected:
(I), (VI) & (IX): All the fractions containing N'-methyl-D-asparaginyl amoxicillin.
(II), (III), (IV), (VII) & (VIII): The fractions containing N'-methyl-D-asparaginyl amoxicillin which were obtained before the elution of the impurity (C) took place.
(V): The fractions containing N'-methyl-D-asparaginyl amoxicillin which were obtained before the elution of the impurity (D) took place.

EXAMPLE 1

(A) Synthesis of N'-methyl-D-asparaginylamoxicillin (1) 89.7 g of D-2-(D-2-o-nitrophenylsulfenylamino-3-N-methylcarbamoyl-propionamido)-2-p-hydroxyphenylacetic acid and 20.2 g of N-methylmorpholine were dissolved in 1,000 ml of dimethylformamide, and a solution of 21.7 g of ethyl chlorocarbonate in 200 ml of tetrahydrofuran was added thereto at −25° to −20° C. under stirring. Then, a solution of 76.4 of 6-aminopenicillanic acid triethylamine salt in 400 ml of water was added to the mixture at −10° to −8° C. The mixture was stirred at −10° to −5° C. for 40 minutes, and further stirred at −5° to 0° C. for 30 minutes. The reaction mixture was adjusted to pH 3 with an aqueous 5% citric acid solution, and extracted with a mixture of 1000 ml of tetrahydrofuran and 500 ml of ethyl acetate. The extract was washed with water, dried and then evaporated at a temperature below 40° C. to remove solvent. The residue was crystallized with ether, whereby 133 g of 6-[D-2-(D-2-o-nitrophenylsulfenylamino-3-N-methylcarbamoyl-propionamido)-2-p-hydroxyphenylacetamido]penicillanic acid were obtained as yellow needles.

M.p. 165°–167° C. (decomp.)

$Ir\nu_{max}^{Nujol}$ (cm$^{-1}$): 3400, 3250, 1780, 1730, 1640 (2) 64.6 g of the product obtained in paragraph (1) and 27.4 g of thiobenzamide were added to 1,000 ml of a mixture of methanol and tetrahydrofuran (4:1), and the mixture was stirred at room temperature for 40 minutes. The reaction mixture was evaporated at a temperature below 30° C. to remove solvent. The residue thus obtained was dissolved in 257.0 ml of water, and 8.0 g of activated charcoal were added thereto, and the mixture was stirred. Said mixture was filtered, and the insoluble materials were washed with a small amount of water. The filtrate and the washing solution were combined. 257.0 ml of an aqueous solution of crude N'-methyl-D-asparaginylamoxicillin were obtained. The aqueous solution contained 150 mg/ml of N'-methyl-D-asparaginylamoxicillin (Purity: 79%).

Figure 1:
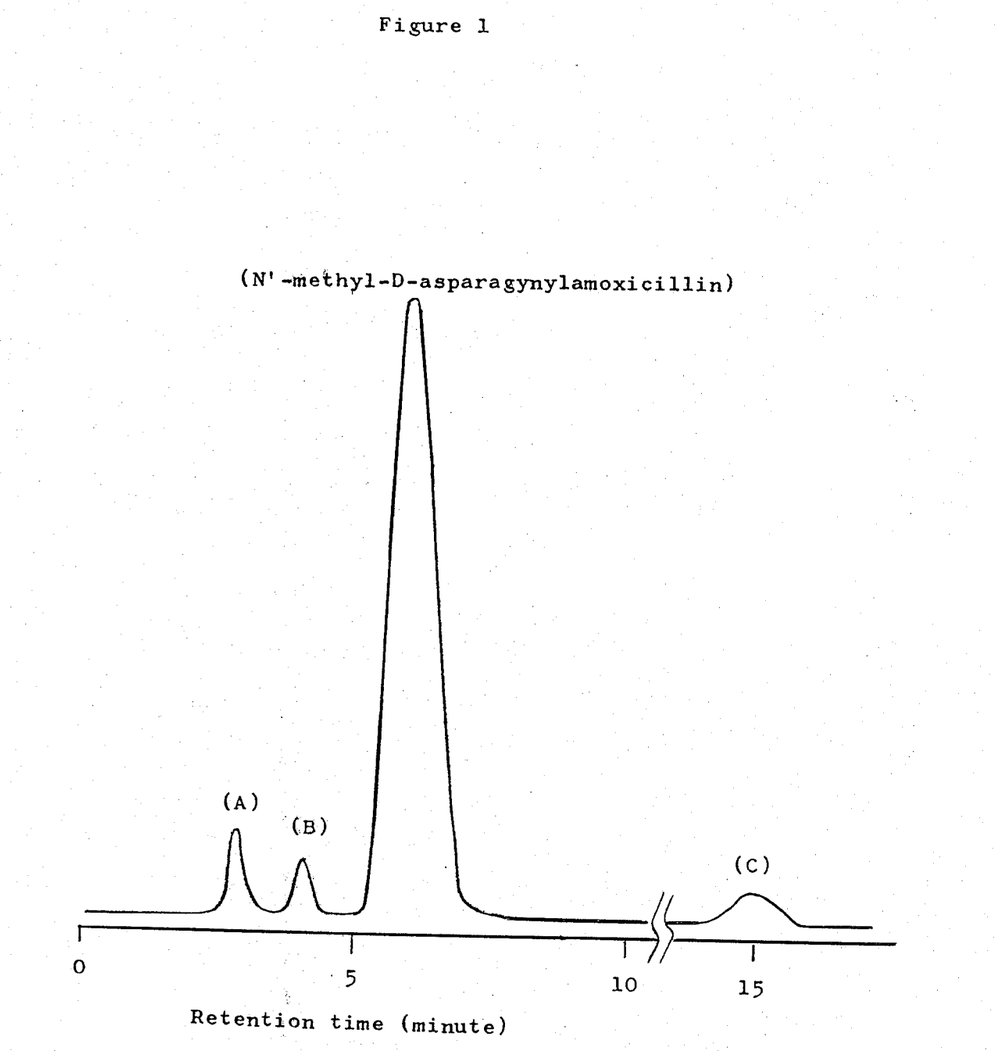
FIG. 1 is the high-performance liquid chromatogram of an aqueous solution of crude N'-methyl-D-asparaginylamoxicillin obtained in Example 1-(A)

High-performance liquid chromatography (Condition A): FIG. 1

(B) Purification of N'-methyl-D-asparaginylamoxicillin

A styrene-divinylbenzene copolymer resin (pore volume: 1.077 ml/g, specific surface area: 718.0 m$^2$/g, particle size: 280 to 370μ manufactured by Mitsubishi Chemical Industries Ltd. under the trade name of "Diaion HP-20") was first swollen with water, and then 800 ml of said resin were charged into a column (5.25 cm in diameter, 37.0 cm in height). 170 ml of the aqueous solution obtained in paragraph (A) (i.e., an aqueous solution of crude N'-methyl-D-asparaginylamoxicillin) were passed through the column to adsorb N'-methyl-D-asparaginylamoxicillin on the resin. Then, water was passed through the column at a space velocity of 2.0 (i.e., at a flow rate of 26.7 ml/minute), and every 900 ml fraction was collected. The substances eluted in each of the fractions exhibited ultraviolet adsorption at 272 nm. The impurities (A) and (B) were eluted into Fraction Nos. 1 and 2, respectively, and N'-methyl-D-asparaginylamoxicillin was eluted into Fraction Nos. 3 through 17. On the other hand, the impurities (C) and (D) were not eluted from the resin during the above-mentioned operations. Fraction Nos. 3 through 17 were combined to obtain 13,500 ml of an aqueous solution containing N'-methyl-D-asparaginylamoxicillin. This aqueous solution contained 1.78 mg/ml of N'-methyl-D-asparagynylamoxicillin.

Recovery yield: 94.1%

High-performance liquid chromatography (Condition A):

No impurity was detected in the aqueous solution. N'-methyl-D-asparaginylamoxicillin was obtained as white powder by freeze drying of the aqueous solution obtained above.

IR$\nu_{max}^{Nujol}$ (cm$^1$): 3280, 1760, 1660

Thin layer chromatography (silica gel, solvent: n-butanol-acetic acid-water (4:1:1): Rf=0.43

EXAMPLE 2

A styrene-divinylbenzene copolymer resin (pore volume: 1.077 ml/g, specific surface area: 718.0 m$^2$/g, particle size: 280 to 370μ) (manufactured by Mitsubishi Chemical Industries Ltd. under the trade name of "Diaion HP-20") was first swollen with water, and then 800 ml of said resin were charged into a column (5.25 cm in diameter, 37.0 cm in height). 167 ml of the aqueous solution obtained in the same manner as described in Example 1-(A) (i.e., an aqueous solution of crude N'-methyl-D-asparaginylamoxicillin) were passed through the column to permit N'-methyl-D-asparaginylamoxicillin to be adsorbed on the resin. After said adsorption of N'-methyl-D-asparagynylamoxicillin on the resin, water (1,800 ml) and 8 v/v % aqueous ethanol were passed successively through the column at a space velocity of 2.0, and every 900 ml of fraction was collected. By the above-mentioned operations, the impurities (A) and (B) were eluted into Fraction Nos. 1 and 2, respectively, and N'-methyl-D-asparaginylamoxicillin was eluted into Fraction Nos. 3 through 6. On the other hand, the impurities (C) and (D) were not eluted from the resin during the operations. Fraction Nos. 3 through 6 were combined to obtain 3,600 ml of an aqueous solution containing pure N'-methyl-D-asparaginylamoxicillin. This aqueous solution contained 6.68 mg/ml of N'-methyl-D-asparaginylamoxicillin.

Recovery yield: 96%

High-performance liquid chromatograph (condition A): No impurity was detected in the aqueous solution.

EXAMPLE 3

A styrene-divinylbenzene copolymer resin (pore volume: 0.687 ml/g, specific surface area: 704.7 m$^2$/g, particle size: 280 to 370μ manufactured by Mitsubishi Chemical Industries Ltd. under the trade name of "Diaion HP-40") was first swollen with water, and then 800 ml of said resin were charged into a column (5.25 cm in diameter, 37.0 cm in height). 167 ml of the aqueous solution obtained in the same manner as described in Example 1-(A) (i.e., an aqueous solution of crude N'-methyl-D-asparaginylamoxicillin) were passed through the column which adsorbed N'-methyl-D-asparaginylamoxicillin on the resin. After said adsorption, water (1,600 ml) and 2.0 v/v % aqueous ethanol were passed successively through the column at a space velocity of 2.0, and every 1,000 ml fraction was collected. By the above-mentioned operations, the impurities (A) and (B) were eluted into Fraction Nos. 1 and 2, respectively, and N'-methyl-D-asparaginylamoxicillin was eluted into Fraction Nos. 3 through 8. On the other hand, the impurities (C) and (D) were not eluted from the resin during the above-mentioned operations. Fraction Nos. 3 through 8 were combined to obtain 6,000 ml of an aqueous solution containing pure N'-methyl-D-asparaginylamoxicillin. This aqueous solution contained 4.03 mg/ml of N'-methyl-D-asparaginylamoxicillin.

Recovery yield: 96.5%

High-performance liquid chromatograph (Condition A): No impurity was detected in the aqueous solution.

EXAMPLE 4

A styrene-divinylbenzene copolymer resin (pore volume: 1.077 ml/g, specific surface area: 718 m$^2$/g, particle size: 280 to 370μ manufactured by Mitsubishi Chemical Industries Ltd. under the trade name of "Diaion HP-20") was first swollen with water, and then 7,693 ml of said resin were charged into a column (14.0 cm in diameter, 50.0 cm in height). 1,667 ml of the aqueous solution obtained in the same manner as described in Example 1-(A) (i.e., an aqueous solution of crude N'-methyl-D-asparaginylamoxicillin) were passed through the column which adsorbed the N'-methyl-D-asparaginylamoxicillin on the resin. Then, water (1,600 ml) and 4 v/v % aqueous ethanol were passed successively through the column at a space velocity of 2.0, and every 7,000 ml fraction was collected. By the above-mentioned operations, the impurities (A) and (B) were eluted into Fraction Nos. 1 and 2, respectively, and N'-methyl-D-asparaginylamoxicillin was eluted into Fraction Nos. 3 through 11. On the other hand, the impurities (C) and (D) were not eluted from the resin during said operations. Fraction Nos. 3 through 11 were combined to obtain 63,000 ml of an aqueous solution containing pure N'-methyl-D-asparaginylamoxicillin. This aqueous solution contained 3.85 mg/ml of N'-methyl-D-asparaginylamoxicillin.

Recovery yield: 97.0%

High-performance liquid chromatograph (Condition A): No impurity was detected in the aqueous solution.

EXAMPLE 5

A styrene-divinylbenzene copolymer resin (pore volume: 0.693 ml/g, specific surface area: 300 m$^2$/g, particle size: 280 to 840μ manufactured by Rohm & Haas Co. under the trade name of "Amberlite XAD-2") was swollen with water, and 800 ml of said resin were charged into a column (5.25 cm in diameter, 37.0 cm in height). 200 ml of the aqueous solution obtained in the same manner as described in Example 1-(A) (i.e., an aqueous solution of crude N'-methyl-D-asparaginylamoxicillin) were passed through the column which absorbed the N'-methyl-D-asparaginylamoxillin on the resin. Then, water (2,000 ml) and 2 v/v % aqueous ethanol were passed successively through the column at a space velocity of 4.0, and every 1,000 ml fraction was collected. By the above-mentioned operations, the impurities (A) and (B) were eluted into Fraction Nos. 1 and 2, respectively, and N'-methyl-D-asparaginylamoxicillin was eluted into Fraction Nos. 3 through 10. On the other hand, the impurities (C) and (D) were not eluted from the resin during said operations. Fraction Nos. 3 through 10 were combined to obtain 8,000 ml of an aqueous solution containing pure N'-methyl-D-asparaginylamoxicillin. This aqueous solution contained 3.60 mg/ml of N'-methyl-D-asparaginylamoxicillin.

Recovery yield: 96.0%

High-performance liquid chromatography (Condition A): No impurity was detected in the aqueous solution.

EXAMPLE 6

(A) Synthesis of N'-methyl-D-asparaginylamoxicillin (1) 1.51 g of N-(D-2-benzyloxycarbonylamino-3-N-methylcarbamoyl-propionyloxy)succinimide and 1.86 g of 6-(D-2-amino-2-p-hydroxyphenylacetamido)penicillanic acid triethylamine salt were dissolved in 10 ml of dimethylformamide. The solution was stirred at 0° to 5° C. for 16 hours. 20 ml of an aqueous 5% citric acid solution were added to the reaction mixture, and the mixture was extracted with a mixture of 40 ml of tetrahydrofuran and 20 ml of ethyl acetate. The extract was washed with water, dried and then evaporated at a temperature below 40° C. to remove solvent. Ether was added to the residue (colorless caramel), and the precipitates were collected by filtration. 2.35 g of 6-[D-2-(D-2-benzyloxycarbonylamino-3-N-methylcarbamoylpropionamido)-2-p-hydroxyphenylacetamido]penicillanic acid were thereby obtained as colorless needles. Yield: 91.1%

IR$\nu_{max}^{Nujol}$(cm$^{-1}$): 3280, 1770, 1720, 1640

Thin layer chromatography (silica gel, solvent: tetrahydrofuran-methanol-acetic acid (50:50:3)): Rf=0.663

(2) 62.7 g of 6-[D-2-(D-2-benzyloxycarbonylamino-3-N-methylcarbamoyl-propionamido)-2-p-hydroxyphenylacetamido]penicillanic acid and 40.0 g of 30% palladium-barium carbonate were suspended in 1,000 ml of methanol. The suspension was shaken at room temperature in hydrogen gas atmosphere under atmospheric pressure for one hour. After the hydrogen uptake was completed, the insoluble materials were removed by filtration. The filtrate was evaporated at a temperature below 40° C. to remove solvent. The residue was dissolved in 250 ml of water, and the aqueous solution was treated with 9 g of activated charcoal. 250 ml of an aqueous solution of crude N'-methyl-D-asparaginylamoxicillin were obtained. The aqueous solution contained 150 mg/ml of N'-methyl-D-asparagynylamoxicillin (Purity: 79%)

Figure 2:
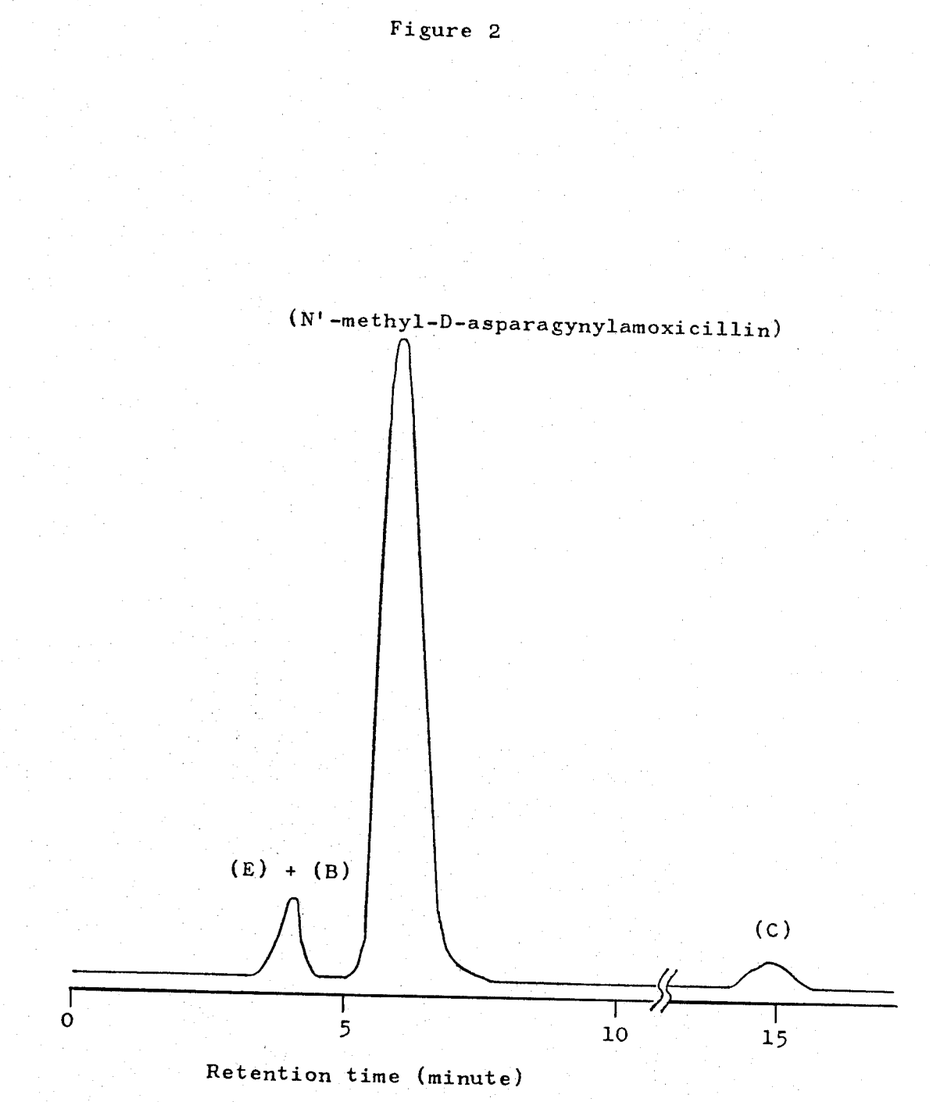
FIGS. 2 and 3 are the high-performance liquid chromatograms of an aqueous solution of crude N'-methyl-D-asparaginylamoxicillin obtained in Example 6-(A).
Figure 3:
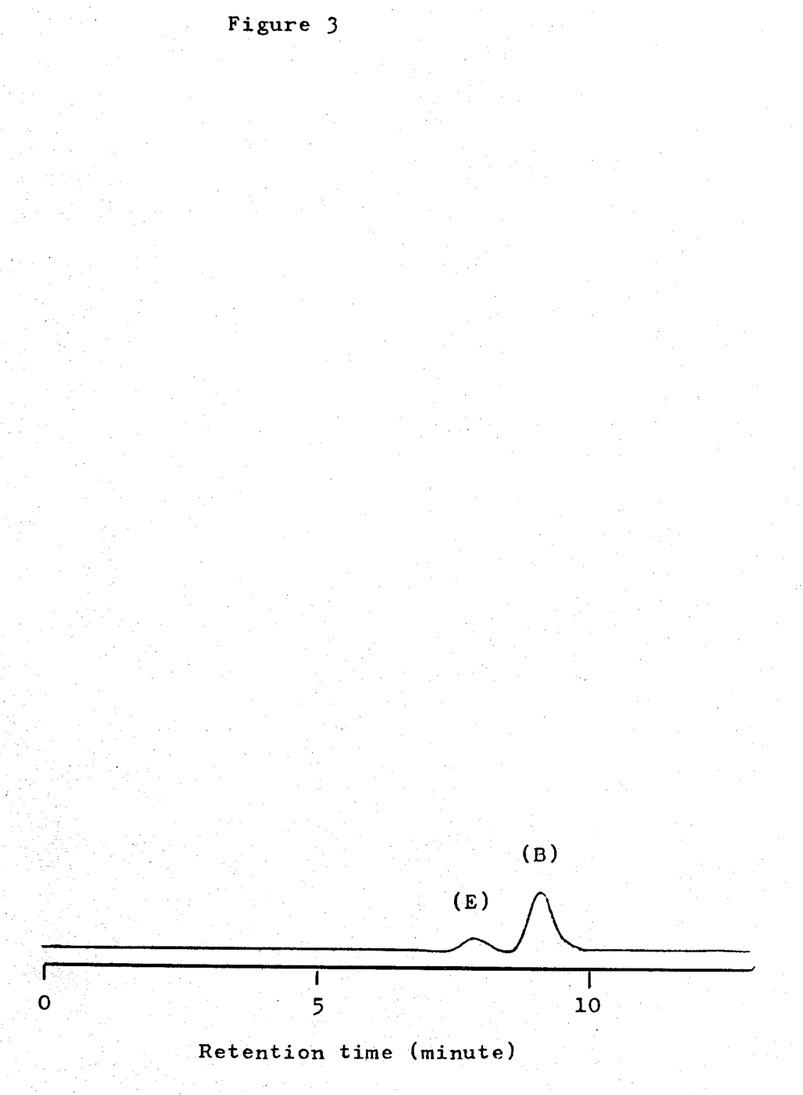

High-performance liquid chromatography: FIG. 2 (Condition A), FIG. 3 (Condition B)

(B) Purification of N'-methyl-D-asparaginylamoxicillin

A styrene-divinylbenzene copolymer resin (pore volume: 1.077 ml/g, specific surface area: 718 m$^2$/g, particle size: 280 to 370μ manufactured by Mitsubishi Chemical Industries Ltd. under the trade name of "Diaion HP-20") was swollen with water, and 800 ml of said resin were charged into a column (5.25 cm in diameter, 37.0 cm in length). 170 ml of the aqueous solution obtained in paragraph (A) (i.e., an aqueous solution of crude N'-methyl-D-asparaginylamoxicillin) were passed through the column which absorbed the N'-methyl-D-asparaginylamoxicillin on the resin. Then, water (1,600 ml) and 2 v/v % aqueous ethanol were passed successively through the column at a space velocity of 2.0, and every 1,000 ml fraction was collected. By the above-mentioned operations, the impurities (B) and (E) were eluted into Fraction Nos. 1 and 2, respectively, and N'-methyl-D-asparaginylamoxicillin was eluted into Fraction Nos. 3 through 8. On the other hand, the impurities (C) and (D) were not eluted from the resin during said operations. Fraction Nos. 3 through 8 were combined to obtain 6,000 ml of an aqueous solution containing pure N'-methyl-D-asparaginylamoxicillin. This aqueous solution contained 4.12 mg/ml of N'-methyl-D-asparaginylamoxicillin.

Recovery yield: 97%

High-performance chromatography (Conditions A & B): No impurity was detected in the aqueous solution.

What we claim is:

1. A method for purification of crude 6-[D-2-(D-2-amino-3-N-methylcarbamoyl-propionamido)-2-p-hydroxyphenylacetamido]penicillanic acid which comprises the steps of:

(A) contacting an aqueous solution of 6-[D-2-(D-2-amino-3-N-methylcarbamoyl-propionamido)-2-p-hydroxyphenylacetamido]penicillanic acid with a nonpolar, macroporous styrenedivinylbenzyl copolymer adsorption resin to absorb 6-[D-2-(D-2-amino-3-N-methylcarbamoyl-propionamido)-2-p-hydroxyphenylacetamido]penicillanic acid on the resin, (B) eluting the absorbed 6-[D-2-(D-2-amino-3-N-methylcarbamoylpropionamido)-2-p-hydroxyphenylacetamido]penicillanic acid with water or a mixture of water and a water-miscible organic solvent, and then (C) isolating pure 6-[D-2-(D-2-amino-3-N-methylcarbamoylpropionamido)-2-p-hydroxyphenylacetamido]penicillanic acid from the eluates.

2. The method according to claim 1, wherein the resin is a styrene-divinylbenzene copolymer having a pore volume of 0.6 to 1.1 ml/g, a specific surface area of 200 to 800 m$^2$/g and a particle size of 45 to 840μ.

3. The method according to claim 2, wherein the mixture of water and a water-miscible organic solvent is a mixture of water and an alkanol having one to 3 carbon atoms.

4. The method according to claim 2, wherein the mixture of water and a water-miscible organic solvent is 2 to 8 v/v % aqueous methanol or 2 to 8 v/v % aqueous ethanol.

5. The method according to claim 2, wherein the concentration of 6-[D-2-(D-2-amino-3-N-methylcarbamoyl-propionamido)-2-p-hydroxyphenylacetamido]-penicillanic acid present in the aqueous solution thereof is 0.5 to 25 w/v %, and the volume of the resin to be used is 3 to 100 ml per gram of 6-[D-2-(D-2-amino-3-N-methylcarbamoyl-propionamido)-2-p-hydroxyphenylacetamido]penicillanic acid present in the aqueous solution.

6. The method according to claim 1, wherein the adsorption and elution steps are carried out by passing said aqueous solution of 6-[D-2-(D-2-amino-3-N-methylcarbamoylpropionamido)-2-p-hydroxyphenylacetamido]penicillanic acid through a column packed with said nonpolar, macroporous styrene-divinylbenzene copolymer adsorption resin at a space velocity of 0.1 to 5 to adsorb 6 -[D-2-(D-2-amino-3-N-methylcarbamoyl-propionamido)-2-p-hydroxyphenylacetamido]penicillanic acid on the resin, and then passing water or a mixture of water and a water-miscible organic solvent through the column at a space velocity of 0.3 to 15 to elute the adsorbed 6-[D-2-(D-2-amino-3-N-methylcarbamoyl-propionamido)-2-p-hydroxyphenylacetamido]penicillanic acid therefrom.

7. The method according to claim 6, wherein the elution step is carried out by passing water through the column at a space velocity of 0.5 to 5.

8. The method according to claim 6, wherein the elution step is carried out by passing the mixture of water and a water-miscible organic solvent through the column at a space velocity of 1 to 3.

9. A method for purification of an aqueous solution containing 6-[D-2-(D-2-amino-3-N-methylcarbamoyl-propionamido)-2-p-hydroxyphenylacetamido]penicillanic acid in admixture with a penicilloic acid, the condensate of said penicillanic and penicilloic acids, colored substances and D-2-(D-2-amino-3-N-methylcarbamoyl-propionamido)-2-p-hydroxyphenylacetic acid (or amoxicillin), which comprises the steps of:
- (A) passing said aqueous solution through a column packed with a nonpolar, macroporous styrene-divinylbenzene copolymer adsorption resin to adsorb 6-[D-2-(D-2-amino-3-N-methylcarbamoyl-propionamido)-2-p-hydroxyphenylacetamido]penicillanic acid on the resin,
- (B) passing water or a mixture of water and a water-miscible organic solvent through the column to elute the adsorbed 6-[D-2-(D-2-amino-3-N-methylcarbamoyl-propionamido)-2-p-hydroxyphenylacetamido]penicillanic acid therefrom, and then,
- (C) isolating pure 6-[D-2-(D-2-amino-3-N-methylcarbamoyl-propionamido)-2-p-hydroxyphenylacetamido]penicillanic acid from the eluates.

10. The method according to claim 9, which comprises the steps of:
- (A) passing said aqueous solution through the column at a space velocity of 0.1 to 5 to adsorb 6-[D-2-(D-2-amino-3-N-methylcarbamoyl-propionamido)-2-p-hydroxyphenylacetamido]penicillanic acid, said penicilloic acid, the condensate of said penicillanic and penicilloic acids, colored substances and D-2-(D-2-amino-3-N-methylcarbamoyl-propionamido)-2-p-hydroxyphenylacetic acid (or amoxicillin) on the resin,
- (B)
  - (a) passing water through the column at a space velocity of 0.3 to 15 to elute the adsorbed 6-[D-2-(D-2-amino-3-N-methylcarbamoyl-propionamido)-2-p-hydroxyphenylacetamido]penicillanic acid therefrom, or
  - (b)
    - (i) washing the column with water to remove D-2-(D-2-amino-3-N-methylcarbamoyl-propionamido)-2-p-hydroxyphenylacetic acid (or amoxicillin) and said penicilloic acid therefrom, and
    - (ii) passing a mixture of water and a water-miscible organic solvent through the column at a space velocity of 0.3 to 5 to elute the adsorbed 6-[D-2-(D-2-amino-3-methylcarbamoyl-propionamido)-2-p-hydroxyphenylacetamido]penicillanic acid therefrom, and then,
- (C) isolating pure 6-[D-2-(D-2-amino-3-N-methylcarbamoyl-propionamido)-2-p-hydroxyphenylacetamido]penicillanic acid from the eluates.

11. The method according to claim 9, wherein the resin is a styrene-divinylbenzene copolymer having a pore volume of 0.6 to 1.1 ml/g, a specific surface area of 200 to 800 m$^2$/g, and a particle size of 45 to 840$\mu$.

12. The method according to claim 10, wherein the concentration of 6-[D-2-(D-2-amino-3-N-methylcarbamoyl-propionamido)-2-p-hydroxyphenylacetamido]penicillanic acid present in the aqueous solution thereof is 0.5 to 25 w/v %, and the volume of the resin to be used is 3 to 100 ml per gram of 6-[D-2-(D-2-amino-3-N-methylcarbamoyl-propionamido)-2-p-hydroxyphenylacetamido]penicillanic acid present in the aqueous solution.

13. The method according to claim 12, wherein the mixture of water and a water-miscible organic solvent is a mixture of water and an alkanol having one to 3 carbon atoms.

14. The method according to claim 12, wherein the mixture of water and a water-miscible organic solvent is 2 to 8 v/v % aqueous methanol or 2 to 8 v/v % aqueous ethanol.

15. The method according to claim 12, wherein the elution of 6-[D-2-(D-2-amino-3-N-methylcarbamoyl-propionamido)-2-p-hydroxyphenylacetamido]penicillanic acid is carried out by passing water through the column at a space velocity of 0.5 to 5.

16. The method according to claim 14, wherein the elution of 6-[D-2-(D-2-amino-3-N-methylcarbamoylamino-propionamido)-2-p-hydroxyphenylacetamido]penicillanic acid is carried out by passing the aqueous methanol or ethanol through the column at a space velocity of 1 to 3.

17. The method according to any one of claims 1–16 wherein said isolating is carried out by condensation, freeze concentration, concentration by reverse osmosis, or freeze drying.

* * * * *